US00PP28223P3

(12) United States Plant Patent
Uchneat

(10) Patent No.: US PP28,223 P3
(45) Date of Patent: Jul. 25, 2017

(54) ***DAHLIA* PLANT NAMED 'G13525'**

(50) Latin Name: *Dahlia variabilis*
Varietal Denomination: G13525

(71) Applicant: Michael S. Uchneat, Bellefonte, PA (US)

(72) Inventor: Michael S. Uchneat, Bellefonte, PA (US)

(73) Assignee: Garden Genetics LLC, Bellefonte, PA (US)

( * ) Notice: Subject to any disclaimer, the term of this patent is extended or adjusted under 35 U.S.C. 154(b) by 0 days.

(21) Appl. No.: 14/756,440

(22) Filed: Sep. 4, 2015

(65) Prior Publication Data

US 2017/0071103 P1 Mar. 9, 2017

(51) Int. Cl.
*A01H 5/02* (2006.01)

(52) U.S. Cl.
USPC ..... Plt./321

(58) Field of Classification Search
USPC ..... Plt./321
See application file for complete search history.

(56) References Cited

PUBLICATIONS

National Gardening Assoc. Plants Database *Dahlia* Dahlightful Sultry Scarlet in the *Dahlias* Database, retrieved on Nov. 1, 2016, retrieved from the Internet at <http://garden.org/plants/view/710314/Dahlia-Dahlia-Dahlightful-Sultry-Scarlet/> pp. 1-3.*
Proven Winners 2016 Dahlightful Sultry Scarlet *Dahlia variabilis,* retrieved on Nov. 1, 2016, retrieved from the Internet at https://www.provenwinners.com/plants/dahlia/dahlightful-sultry-scarlet-dahlia-variabilis pp. 1-3.*

* cited by examiner

*Primary Examiner* — June Hwu
(74) *Attorney, Agent, or Firm* — C. A. Whealy

(57) ABSTRACT

A new and distinct cultivar of *Dahlia* plant named 'G13525', characterized by its compact and upright plant habit; vigorous growth habit; freely branching habit; black-colored leaves; early and freely flowering habit; and semi-double type inflorescences with greyed red-colored ray florets.

1 Drawing Sheet

Botanical designation: *Dahlia variabilis.*
Cultivar denomination: 'G13525'.

BACKGROUND OF THE INVENTION

The present invention relates to a new and distinct cultivar of *Dahlia* plant, botanically known as *Dahlia variabilis* and hereinafter referred to by the name 'G13525'.

The new *Dahlia* plant is a product of a planned breeding program conducted by the Inventor in Bellefonte, Pa. The objective of the breeding program is to create new vigorous *Dahlia* plants that have dark-colored leaves, large attractive inflorescences and reduced sensitivity to Powdery Mildew.

The new *Dahlia* plant originated from an open-pollination in Bellefonte, Pa. in October, 2012 of a proprietary selection of *Dahlia variabilis* identified as code number 3180-5M-6, not patented, as the female, or seed, parent with an unidentified proprietary selection of *Dahlia variabilis*, as the male, or pollen, parent. The new *Dahlia* plant was discovered and selected by the Inventor as a single flowering plant from within the progeny of the stated open-pollination in a controlled greenhouse environment in Bellefonte, Pa. in July, 2013.

Asexual reproduction of the new *Dahlia* plant by vegetative terminal cuttings in a controlled greenhouse environment in Bellefonte, Pa. since August, 2013 has shown that the unique features of this new *Dahlia* plant are stable and reproduced true to type in successive generations.

SUMMARY OF THE INVENTION

Plants of the new *Dahlia* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'G13525'. These characteristics in combination distinguish 'G13525' as a new and distinct *Dahlia* plant:

1. Compact and upright plant habit.
2. Vigorous growth habit.
3. Freely branching habit.
4. Black-colored leaves.
5. Early and freely flowering habit.
6. Semi-double type inflorescences with greyed red-colored ray florets.

Compared to plants of the female parent selection, plants of the new *Dahlia* differ primarily in the following characteristics:

1. Plants of the new *Dahlia* have darker-colored leaves than plants of the female parent selection.
2. Plants of the new *Dahlia* have larger inflorescences than plants of the female parent selection.
3. Plants of the new *Dahlia* have semi-double type inflorescences whereas plants of the female parent selection have single type inflorescences.
4. Plants of the new *Dahlia* and the female parent selection differ in ray floret color as plants of the female parent selection have red-colored ray florets.

Plants of the new *Dahlia* can be compared to plants of *Dahlia* 'Mystic Wonder', disclosed in U.S. Plant Pat. No.

24,397. In side-by-side comparisons conducted in Bellefonte, Pa., plants of the new *Dahlia* differed primarily from plants of 'Mystic Wonder' in the following characteristics:

1. Plants of the new *Dahlia* were more compact than plants of 'Mystic Wonder'.
2. Plants of the new *Dahlia* were more freely branching than plants of 'Mystic Wonder'.
3. Plants of the new *Dahlia* had semi-double type inflorescences whereas plants of 'Mystic Wonder' had single type inflorescences.
4. Plants of the new *Dahlia* and 'Mystic Wonder' differed in ray floret color as plants of 'Mystic Wonder' had rich red-colored ray florets.

Plants of the new *Dahlia* can be compared to plants of *Dahlia* 'HS Romeo', disclosed in U.S. Plant Pat. No. 17,961. In side-by-side comparisons conducted in Bellefonte, Pa., plants of the new *Dahlia* differed primarily from plants of 'HS Romeo' in the following characteristics:

1. Plants of the new *Dahlia* were more freely branching than plants of 'HS Romeo'.
2. Plants of the new *Dahlia* had semi-double type inflorescences whereas plants of 'HS Romeo' had single type inflorescences.
3. Plants of the new *Dahlia* and 'HS Romeo' differed in ray floret color as plants of 'HS Romeo' had dark red purple-colored ray florets.

BRIEF DESCRIPTION OF THE PHOTOGRAPHS

The accompanying photographs illustrate the overall appearance of the new *Dahlia* plant showing the colors as true as it is reasonably possible to obtain in colored reproductions of this type. Colors in the photographs may differ slightly from the color values cited in the detailed botanical description which accurately describe the colors of the new *Dahlia* plant.

The photograph at the bottom of the sheet is a side perspective view of a typical flowering plant of 'G13525' grown in a container.

The photograph at the top of the sheet is a close-up view of a typical flowering plant of 'G13525'.

DETAILED BOTANICAL DESCRIPTION

The aforementioned photographs and the following observations and measurements describe plants grown during the summer in 10-cm containers in an outdoor nursery in Bonsall, Calif. and under cultural practices typical of commercial potted *Dahlia* production. During the production of the plants, day temperatures averaged 27° C., night temperatures averaged 18° C. and light levels ranged from 7,000 to 10,000 foot-candles. Plants were pinched one time and were seven weeks old when the photographs and description were taken. In the following description, color references are made to The Royal Horticultural Society Colour Chart, 2007 Edition, except where general terms of ordinary dictionary significance are used.

Botanical classification: *Dahlia variabilis* 'G13525'.

Parentage:

*Female, or seed, parent.*—Proprietary selection of *Dahlia variabilis* identified as code number 3180-5M-6, not patented.

*Male, or pollen, parent.*—Unidentified proprietary selection of *Dahlia variabilis*, not patented.

Propagation:

*Type.*—By vegetative terminal cuttings.

*Time to initiate roots, summer.*—About 7 to 10 days at ambient temperatures about 22° C. to 27° C.

*Time to initiate roots, winter.*—About 10 to 14 days at ambient temperatures about 18° C. to 23° C.

*Time to produce a rooted plant, summer.*—About three to four weeks at ambient temperatures about 22° C. to 27° C.

*Time to produce a rooted plant, winter.*—About four weeks at temperatures about 18° C. to 23° C.

*Root description.*—Medium in thickness, fleshy and fibrous; close to white to creamy white in color, actual color of the roots is dependent on substrate composition, water quality, fertilizers, substrate temperature and age of roots; tuber development has not been observed on plants of the new *Dahlia*.

*Rooting habit.*—Freely branching; medium density.

Plant description:

*Plant and growth habit.*—Compact and upright plant form; inverted triangle; freely branching habit with about three to four lateral branches developing per plant, each lateral with potentially two secondary laterals developing per node; pinching enhances lateral branch development; inflorescences held above the foliar plane on strong peduncles; vigorous growth habit.

*Plant height.*—About 21 cm.

*Plant diameter or spread.*—About 19.5 cm.

*Lateral branches.*—Length: About 16 cm. Diameter: About 4 mm. Internode length: About 1.5 cm. Strength: Strong. Aspect: Erect. Texture: Smooth, glabrous. Luster: Matte. Color: Close to 187A.

Leaf description:

*Arrangement.*—Opposite; simple.

*Length.*—About 7 cm.

*Width.*—About 7.8 cm.

*Shape.*—Deeply three to five-lobed with parallel to divergent sinuses.

*Apex.*—Acute.

*Base.*—Attenuate.

*Margin.*—Serrate.

*Venation pattern.*—Pinnate.

*Texture, upper and lower surfaces.*—Smooth, glabrous; leathery.

*Luster, upper and lower surfaces.*—Matte.

*Color.*—Developing leaves, upper surface: Close to 146A. Developing leaves, lower surface: Close to 197B. Fully expanded leaves, upper surface: Close to 203A; venation, close to 203A. Fully expanded leaves, lower surface: Close to N200B; venation, close to 200A.

*Petioles.*—Length: About 4.1 cm. Diameter: About 4 mm. Strength: Strong. Texture, upper and lower surfaces: Smooth, glabrous. Luster, upper and lower surfaces: Glossy. Color, upper and lower surfaces: Close to 200A.

Inflorescence description:

*Appearance and arrangement.*—Semi-double inflorescence form with ray florets forming acropetally on a receptacle; inflorescences positioned above the foliar plane on strong peduncles; inflorescences face mostly upright to outwardly; freely flowering habit with about ten inflorescence buds and open inflorescences at one time.

*Fragrance.*—Faint; slightly sour.

*Time to flower*.—Early flowering habit, plants begin flowering about five weeks after planting; plants flower continuously from late spring through the autumn in Southern California.

*Post-production longevity*.—Inflorescences maintain good substance for about five days on the plant; inflorescences persistent.

*Inflorescence buds*.—Height: About 1.2 cm. Diameter: About 1.4 cm. Shape: Ovoid to spherical. Color: Close to 179C to 179D.

*Inflorescence size*.—Diameter: About 5.7 cm. Depth (height): About 2.3 cm. Disc diameter: About 1.7 cm.

*Receptacles*.—Height: About 1 cm. Diameter: About 3.8 cm. Shape: Shallow bowl-shape. Color: Close to 202A and 183A to 183B.

*Ray florets*.—Quantity per inflorescence: About 26 arranged in three whorls. Length: About 2.6 cm. Width: About 1.8 cm. Shape: Obovate. Apex: Apiculate. Base: Attenuate. Margin: Entire. Aspect: Initially upright to roughly perpendicular to the peduncle; somewhat concave. Texture, upper and lower surfaces: Longitudinally ridged, glabrous. Luster, upper and lower surfaces: Matte, velvety. Color: When opening, upper surface: Close to 180C. When opening, lower surface: Close to 179D. Fully opened, upper surface: Close to 179A to 179B; color becoming closer to 171A to 171B with development. Fully opened, lower surface: Close to 179B to 179C; color becoming closer to 171C to 171D with development.

*Disc florets*.—Quantity per inflorescence: About 54. Length: About 1.4 cm. Diameter: About 2.5 mm. Shape: Tubular, elongated; apices acute. Texture: Smooth, glabrous. Luster: Satiny. Color, when opening: Apex: Close to 187A. Mid-section: Close to 183B. Base: Close to 145B. Color, fully opened: Apex: Close to 187A. Mid-section: Close to 185A. Base: Close to 147D.

*Phyllaries*.—Quantity per inflorescence: About 40 arranged in about four to five whorls. Inner whorls: Length: About 1.4 cm. Width: About 5 mm. Shape: Elliptical. Apex: Broadly acute. Base: Truncate. Margin: Entire. Texture, upper and lower surfaces: Smooth, glabrous; membranous, thin. Luster, upper and lower surfaces: Glossy. Color, upper and lower surfaces: Close to 146D; translucent. Outer whorl: Quantity: About 5-10. Length: About 1.7 cm. Width: About 6 mm. Shape: Elliptical. Apex: Broadly acute. Base: Truncate. Margin: Entire. Texture, upper and lower surfaces: Smooth, glabrous. Luster, upper and lower surfaces: Glossy. Color, upper surface: Close to 187A to 187B. Color, lower surface: Close to 183A.

*Peduncles*.—Length, terminal peduncle: About 5.7 cm. Diameter: About 2 mm. Aspect: Mostly erect. Strength: Strong. Texture: Smooth, glabrous. Luster: Matte. Color: Close to 202A.

*Reproductive organs*.—Present on disc florets only; ray florets without visible reproductive organs. Androecium: Quantity per floret: Five. Filament length: About 7 mm. Filament color: Close to 145D. Anther shape: Lanceolate. Anther length: About 3 mm. Anther color: Close to 22A. Pollen amount: Scarce. Pollen color: Close to 22A. Gynoecium: Quantity per floret: One. Pistil length: About 1.9 cm. Style length: About 9 mm. Style color: Close to 1A. Stigma shape: Bi-parted. Stigma color: Close to 15A. Ovary color: Close to 146D. Seeds and fruits: Seed and fruit development have not been observed on plants of the new *Dahlia*.

Disease & pest resistance: Plants of the new *Dahlia* have not been observed to be resistant to pathogens and pests common to *Dahlia* plants.

It is claimed:

1. A new and distinct *Dahlia* plant named 'G13525' as illustrated and described.

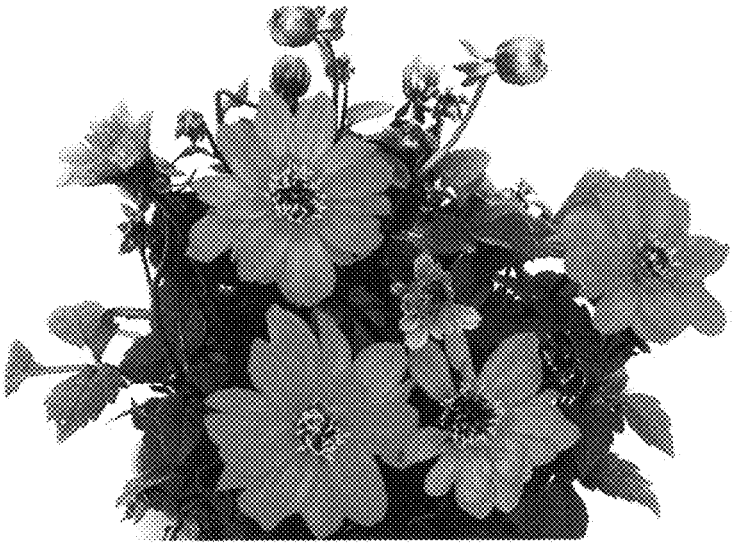
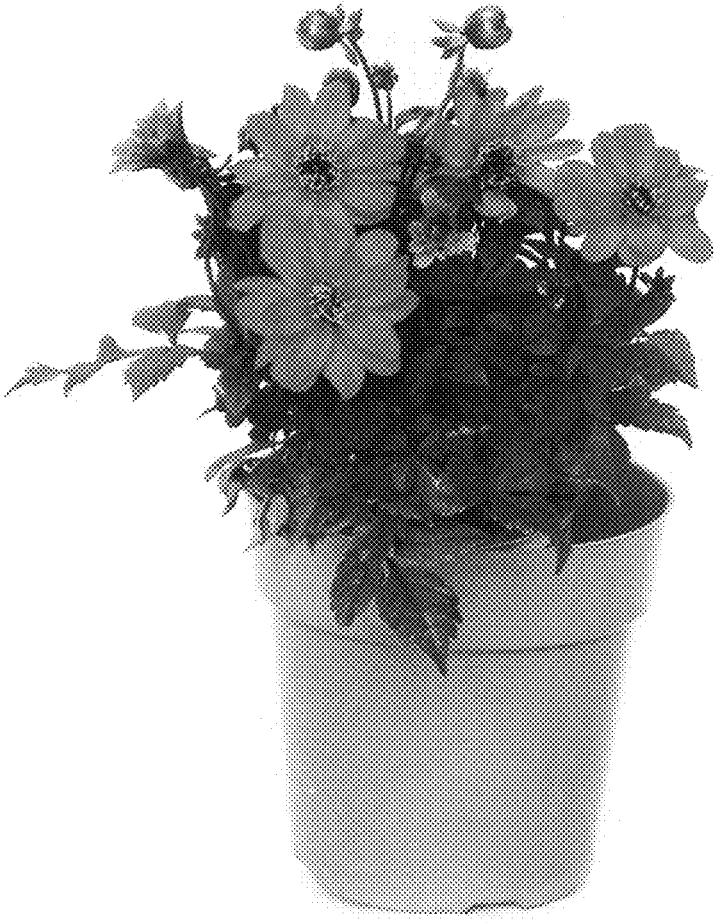

* * * * *